US011413122B2

(12) United States Patent
Rothbrust et al.

(10) Patent No.: US 11,413,122 B2
(45) Date of Patent: Aug. 16, 2022

(54) CONTROLLING OF SINTERING KINETICS OF OXIDE CERAMICS

(71) Applicant: Ivoclar Vivadent AG, Schaan (LI)

(72) Inventors: Frank Rothbrust, Frastanz (AT);
Christian Ritzberger, Grabs (CH);
Dmitri Brodkin, Livingston, NJ (US);
Ajmal Khan, Princeton, NJ (US);
Marcel Schweiger, Chur (CH)

(73) Assignee: Ivoclar Vivadent AG, Schaan (LI)

( * ) Notice: Subject to any disclaimer, the term of this patent is extended or adjusted under 35 U.S.C. 154(b) by 9 days.

(21) Appl. No.: 16/167,730

(22) Filed: Oct. 23, 2018

(65) Prior Publication Data

US 2019/0099245 A1    Apr. 4, 2019

Related U.S. Application Data

(62) Division of application No. 14/906,045, filed as application No. PCT/EP2014/065595 on Jul. 21, 2014, now abandoned.

(30) Foreign Application Priority Data

Jul. 22, 2013   (EP) .................................. 13177474

(51) Int. Cl.
*A61C 13/00*   (2006.01)
*B32B 18/00*   (2006.01)
(Continued)

(52) U.S. Cl.
CPC ............ *A61C 13/0022* (2013.01); *A61K 6/61* (2020.01); *B28B 1/008* (2013.01); *B32B 5/16* (2013.01);
(Continued)

(58) Field of Classification Search
CPC ....... B28B 3/10; B28B 1/008; A61C 13/0022; A61C 13/081; C04B 2237/66; C04B 35/62813
See application file for complete search history.

(56) References Cited

U.S. PATENT DOCUMENTS 5,011,403 A    4/1991   Sadoun et al.
5,263,858 A    11/1993  Yoshida et al.
(Continued)

FOREIGN PATENT DOCUMENTS

JP    09057903 A   *  3/1997
WO    0115620 A1      3/2001
(Continued)

OTHER PUBLICATIONS

JP H09-57903 A (Kimura) Mar. 4, 1997 (English language machine translation), [online] [retrieved Dec. 20, 2019]. Retrieved from: Espacenet. (Year: 1997).*

(Continued)

*Primary Examiner* — Erin Snelting
(74) *Attorney, Agent, or Firm* — Ann M. Knab; Thad McMurray

(57) ABSTRACT

The invention relates to multi-layer oxide ceramic bodies and in particular to presintered multi-layer oxide ceramic blanks and oxide ceramic green bodies suitable for dental applications. These bodies can be thermally densified by further sintering without distortion and are thus particularly suitable for the manufacture of dental restorations. The invention also relates to a process for the manufacture of such multi-layer oxide ceramic bodies as well as to a process for the manufacture of dental restorations using the multi-layer oxide ceramic bodies.

16 Claims, 6 Drawing Sheets

(51) Int. Cl.
  *B28B 1/00* (2006.01)
  *C04B 35/486* (2006.01)
  *A61K 6/61* (2020.01)
  *B32B 7/023* (2019.01)
  *B32B 5/16* (2006.01)
  *C04B 35/48* (2006.01)

(52) U.S. Cl.
  CPC .............. *B32B 7/023* (2019.01); *B32B 18/00* (2013.01); *C04B 35/48* (2013.01); *C04B 35/486* (2013.01); *B32B 2264/102* (2013.01); *B32B 2264/107* (2013.01); *B32B 2307/536* (2013.01); *B32B 2307/732* (2013.01); *B32B 2535/00* (2013.01); *C04B 2235/327* (2013.01); *C04B 2235/3217* (2013.01); *C04B 2235/3224* (2013.01); *C04B 2235/3225* (2013.01); *C04B 2235/3246* (2013.01); *C04B 2235/3265* (2013.01); *C04B 2235/3272* (2013.01); *C04B 2235/5409* (2013.01); *C04B 2235/604* (2013.01); *C04B 2235/6026* (2013.01); *C04B 2235/612* (2013.01); *C04B 2235/6562* (2013.01); *C04B 2235/96* (2013.01); *C04B 2235/9615* (2013.01); *C04B 2235/9661* (2013.01); *C04B 2237/348* (2013.01); *C04B 2237/58* (2013.01); *C04B 2237/66* (2013.01); *C04B 2237/78* (2013.01)

(56) References Cited

U.S. PATENT DOCUMENTS

| | | | |
|---|---|---|---|
| 5,656,564 | A | 8/1997 | Nakayama et al. |
| 6,379,593 | B1 | 4/2002 | Datzmann et al. |
| 6,576,182 | B1 | 6/2003 | Ravagni et al. |
| 6,709,694 | B1 | 3/2004 | Suttor et al. |
| 6,713,421 | B1 | 3/2004 | Hauptmann et al. |
| 8,844,139 | B2 | 9/2014 | Johnson et al. |
| 2004/0119180 | A1 | 6/2004 | Frank |
| 2004/0245663 | A1 | 12/2004 | MacDougald et al. |
| 2007/0272120 | A1 | 11/2007 | Engels et al. |
| 2007/0292597 | A1 | 12/2007 | Ritzberger et al. |
| 2008/0064011 | A1 | 3/2008 | Rheinberger et al. |
| 2008/0274440 | A1 | 11/2008 | Smith et al. |
| 2010/0047438 | A1 | 2/2010 | Bissinger et al. |
| 2010/0216095 | A1 | 8/2010 | Scharf |
| 2011/0189636 | A1 | 8/2011 | Thiel et al. |
| 2012/0139141 | A1 | 6/2012 | Khan et al. |
| 2012/0238437 | A1* | 9/2012 | Torrecillas San Millan ................ B82Y 30/00 501/134 |
| 2013/0069264 | A1 | 3/2013 | Giordano |
| 2013/0221554 | A1 | 8/2013 | Jung et al. |
| 2015/0246459 | A1 | 9/2015 | Dorn et al. |
| 2016/0081777 | A1 | 3/2016 | Yamada et al. |

FOREIGN PATENT DOCUMENTS

| | | |
|---|---|---|
| WO | 0209612 A1 | 2/2002 |
| WO | 2007137696 A2 | 12/2007 |

OTHER PUBLICATIONS

Denry, Isabelle et al., "State of the art of zirconia for dental applications," Dental Materials, 2008, vol. 24, pp. 299-307.

Hannink, Richard et al., "Transformation Toughening in Zirconia-Containing Ceramics," J. Am. Ceram. Soc., 2000, vol. 83, No. 3, pp. 461-497.

International Preliminary Report on Patentability of PCT/EP2014/065595, dated Jan. 26, 2016, 10 pages.

* cited by examiner

CONTROLLING OF SINTERING KINETICS OF OXIDE CERAMICS

CROSS-REFERENCE TO RELATED APPLICATIONS

This application claims priority to and is a divisional application of U.S. application Ser. No. 14/906,045, filed on Jan. 19, 2016, which is the National Stage application of International Patent Application No. PCT/EP2014/065595 filed on Jul. 21, 2014, which claims priority to European Patent Application No. 13177474.7 filed on Jul. 22, 2013, the disclosures of which are incorporated herein by reference in their entirety.

FIELD OF THE INVENTION

The invention relates to multi-layer oxide ceramic bodies and in particular to presintered oxide ceramic blanks and oxide ceramic green bodies for dental applications. These bodies can be thermally densified by further sintering without distortion and are thus particularly suitable for the manufacture of dental restorations having excellent mechanical properties and very high accuracy of fit while allowing to closely imitate the optical properties of natural teeth. The invention also relates to a process for the manufacture of such multi-layer oxide ceramic bodies as well as to a process for the manufacture of dental restorations using the multi-layer oxide ceramic bodies.

BACKGROUND

For many years oxide ceramic materials have been used for the preparation of dental implants and restorations. Such ceramics are typically based on zirconia in the form of tetragonal zirconia polycrystals (TZP). Pure $ZrO_2$ undergoes a tetragonal to monoclinic phase transformation at temperatures below 950° C. that is accompanied by a substantial increase in volume. Maintaining zirconia in its tetragonal form at ambient temperature requires the use of additives such as $Y_2O_3$, $CeO_2$, MgO or CaO. These additives inhibit the tetragonal to monoclinic transformation, thereby resulting in a metastable state in which zirconia is fully or partially in its tetragonal form. When cracks form in such metastable tetragonal zirconia ceramics, the strain at the crack tip triggers a local transformation from the tetragonal to the monoclinic form, and the volume increase associated therewith efficiently opposes crack propagation. This so-called transformation toughening mechanism provides for high toughness of stabilized zirconia ceramics (Hannink et al., J. Am. Ceram. Soc. 2000, 83, 461-487). This, together with the bio-inertness of zirconia, has led to the use of doped TZP in orthopedics and dental restorations. Today, particularly tetragonal zirconia polycrystals stabilized with $Y_2O_3$ (Y-TZP), typically with addition of $Al_2O_3$ (about 0.25 wt.-%), are widely used as an all-ceramic dental biomaterial (Denry et al., Dental Materials 2008, 24, 299-307).

Different methods for the manufacture of ceramics are known. Preferred methods include (i) uniaxial pressing or cold isostatic pressing (CIP) followed by conventional sintering, (ii) slip casting followed by conventional sintering, and (iii) hot pressing (HP) or hot isostatic pressing (HIP).

For dental applications, the preparation of ceramic materials often comprises two densification steps separated by a shaping step. Accordingly, a ceramic material can be pressed or cast and then presintered to an intermediate open porous state. Then, a shaping or preshaping of the ceramic material can be carried out, followed by a final thermal densification by further sintering.

In order to enhance the aesthetic appearance of dental restorations, ceramics for use as dental restorative materials often need to be provided with coloration. A number of ways to colorize ceramic materials are known.

One approach towards obtaining colored dental ceramic materials uses a coloring of a ceramic material in the porous state by infiltration of metal compound solutions. Typically the process comprises the steps of drying the porous structure, fully or partly infiltrating the porous structure with a coloring solution, cleaning the surface and drying the infiltrated structure, optionally infiltrating the porous structure with a further coloring solution, and finally sintering.

The patents and patent applications below describing the relevant processes and methods are included in their entirety by reference herein.

U.S. Pat. No. 6,709,694 B1 describes a process for coloring oxide ceramics in the porous or absorbent state with solutions of salts or complexes of transition metals.

EP 1 486 476 A1 describes a process for coloring presintered ceramic bodies using a solution comprising a metal salt, a solvent and a polyethylene glycol having a $M_n$ in the range of 1.000 to 200.000.

This approach suffers from the complicated process for the dental technician and the low homogeneity of the obtained color distribution. Furthermore, depending on the concentration of the coloring ions, the enlargement factor can change within the colored layer, which leads to stresses between the colored and non-colored portions during the final sintering step.

Another approach involves the precoloring of a zirconia powder via a coprecipitation of zirconia together with coloring substances or by contacting a zirconia powder with solutions of coloring substances to achieve precolored primary and secondary particles of varying powder characteristics.

U.S. Pat. No. 5,011,403 A describes the preparation of a colored bracket by compressing and sintering a powder obtained by adding coloring transition metal oxides into a partially stabilized zirconium oxide powder, wherein the transition metal oxides are incorporated either in powdered form or by atomizing the zirconium oxide powder with a solution of water-soluble salts of the transition metal oxides.

U.S. Pat. No. 5,263,858 A describes the preparation of an ivory-colored sintered zirconia body that can be used as a bracket for orthodontic application, which process comprises preparing a mixed powder by (A) coprecipitation of a solution containing compounds of zirconium, a stabilizer, erbium and praseodymium and calcination or (B) mixing solutions of erbium and praseodymium compounds with a zirconia powder containing a stabilizer, forming a shaped body from the resultant powder and sintering.

U.S. Pat. No. 5,656,564 A describes colored sintered zirconia bodies for orthodontic bracket materials which are prepared by wet mixing a stabilized zirconia powder with colorants, molding the obtained powder and sintering.

U.S. Pat. No. 6,713,421 A describes blanks based on a ceramic composition comprising zirconium oxide, at least one of the oxides of aluminum, gallium, germanium and indium and further comprising coloring additives. The ceramic composition is prepared by coprecipitation and calcination.

Yet another approach involves the coloring of ready-to-press ceramic powders by coating techniques.

US 2007/292597 A1 describes a process for the preparation of single- and multi-colored blanks and dental shaped parts, which process comprises coating an oxide powder with a coloring substance, pressing the colored powder to produce a shaped body and sintering the compressed shaped body.

US 2008/0274440 A1 describes a dental implant abutment comprising a single unit structure for supporting a dental prosthesis which is fabricated of a ceramic material and which is shaded to match the color of the dental prosthesis and the surrounding dentition and gingival tissue. The shading of the abutment can be achieved inter alia by coating an oxide powder with coloring substances according to US 2007/292597 A1.

Still another approach involves coloring by mixing and blending of colored and non-colored powders and pigments.

U.S. Pat. No. 6,379,593 describes a method for the manufacture of a multi-colored shaped body suitable for further processing to form a dental restoration, which method comprises successively introducing differently colored ceramic materials into a compacting die, pressing into the form of a shaped body and sintering.

US 2007/272120 A1 describes a ceramic block comprising first and second ceramic compounds with different optical properties and further comprising a transition area between the ceramic compounds wherein the variation gradient of the resulting optical properties is substantially constant.

US 2008/064011 A1 describes a multi-colored shaped body having differently colored main layers and intermediate layers, wherein a change in color between the intermediate layers takes place in a direction which is contrary to the direction of the change in color between the main layers. Also disclosed is a multi-colored shaped body having differently colored main layers and an intermediate layer comprising a mixture of the materials of the main layers.

WO 2008/083358 A1 describes a multicolor dental blank having concentric inner and outer zones of different coloration.

US 2010/0216095 A1 describes the manufacture of shaded dental ceramics by mixing Y-TZP with coloring components to obtain substantially homogenous shaded aggregate materials, mixing differently shaded aggregate materials, pressing and sintering.

US 2011/0189636 A1 describes molded bodies comprising differently colored first and second components, wherein the second component is arranged within the first component to form a curved interface.

US 2012/139141 A1 describes the preparation of shaded zirconium oxide articles by treating an Y-TZP powder with a solution of coloring agents to obtain a pigmented powder, mixing the pigmented powder with an uncolored powder, pressing the mixed powder and sintering.

These prior art techniques have been found to suffer from the problem of differing and incompatible sintering kinetics of the different ceramic powders used therein, such as combinations of colored and uncolored powders or combinations of differently colored powders. When different powders are combined to form the different layers of a multi-layer ceramic body, these differences in sintering kinetics will result in a distortion of the body upon sintering. Such a distortion is particularly unsuitable for dental applications.

SUMMARY

In view of the above, there is a need to overcome the above described disadvantages of the prior art. It is thus an object of the invention to provide a multi-layer oxide ceramic bodies and in particular oxide ceramic blanks comprising differently colored layers that show no distortion during the thermal densification step, and in particular to provide ceramic bodies that are useful for the manufacture of dental articles with high accuracy of fit, reliable and easy processing for the dental technician and a very high aesthetic appearance of the finally densified ceramic.

BRIEF DESCRIPTION OF THE DRAWINGS

Further advantages, details and features may be taken from the following description in conjunction with the drawings, in which.

DETAILED DESCRIPTION

Figure 1:
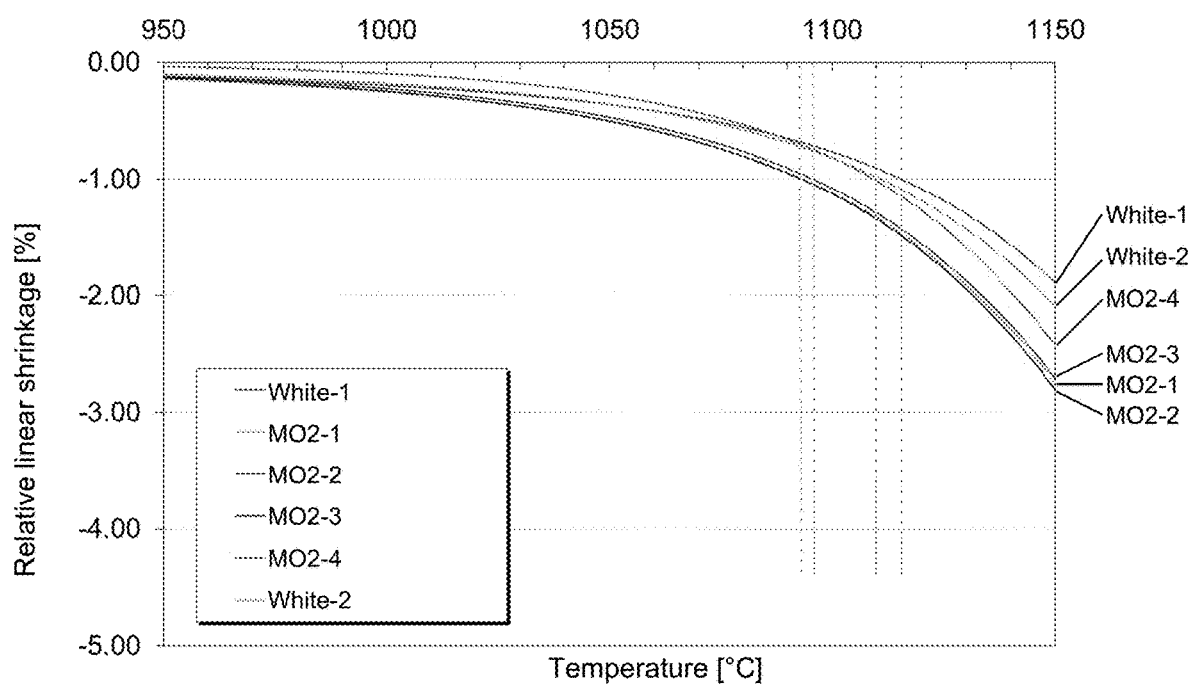
FIG. 1 shows a plot of the relative shrinkage as a function of temperature.

According to a first aspect of the present invention, this problem is solved by a presintered multi-layer oxide ceramic blank for dental applications comprising at least two different layers and having a coefficient of distortion $$d = \frac{(HV_{max} - HV_{min})}{\overline{HV}}$$

of less than 0.4, particularly less than 0.35, more particularly less than 0.3, preferably less than 0.25, more preferably less than 0.2 and most preferably less than 0.1, which coefficient is calculated on the basis of at least one measurement of $HV_{2.5}$ for each of the different layers, wherein:

$HV_{2.5}$ is the Vickers hardness measured at a load of 2.5 kgf (24.517 N) according to ISO 14705:2008;

$HV_{max}$ is the maximum of the measured values of $HV_{2.5}$;

$HV_{min}$ is the minimum of the measured values of $HV_{2.5}$; and $\overline{HV}$ is the arithmetic mean of the measured values of $HV_{2.5}$.

It has surprisingly been found that the blanks according to the invention show no or essentially no distortion during the final sintering step. In particular, they do not suffer from significant differences in sintering kinetics or shrinkage behavior between the different layers. Moreover, the measurement of Vickers hardness according to the standard ISO 14705:2008 was unexpectedly found to be suitable to identify and predict the sintering behavior of different locations within a presintered multi-layer blank.

The blank according to the present invention is preferably suitable for the manufacture of a multi-unit dental restoration, more preferably a dental restoration spanning two or more units, and in particular a bridge spanning two or more units.

The blank comprises at least two layers, which are preferably planar layers that are arranged on top of one another in a parallel manner. The blank is preferably in the form of a rectangular block, a disc, a cylinder, a dental preshape, an abutment preshape, a tooth sector, a horseshoo, a cone, a cone segment, a pyramid, a pyramid segment, a torus, a torus segment, a conical frustum, a conical frustum segment, a tube, a tube segment, a sphere, a spherical segment, an ellipsoid or an ellipsoid segment, in each case with or without notch or ledge.

Oxide ceramics are generally highly crystalline ceramic materials which are based on oxide compounds and include a very low, if any, amount of glass phase. Typical oxide ceramics are based on $ZrO_2$, $Al_2O_3$, $TiO_2$, MgO, combinations, solid solutions and composites thereof. Oxide ceramics based on $ZrO_2$ and/or $Al_2O_3$ are particularly preferred.

Oxide ceramics based on zirconia and more particularly based on tetragonal zirconia polycrystals (TZP) which are suitably stabilized for instance by $Y_2O_3$, $CeO_2$, MgO and/or CaO are even more preferred. Particularly preferred oxide ceramics include yttria stabilized tetragonal zirconia polycrystals (Y-TZP), ceria stabilized tetragonal zirconia polycrystal (Ce-TZP), zirconia toughened alumina (ZTA) and alumina toughened zirconia (ATZ).

It is particularly preferred that the total amount of $ZrO_2$, $Y_2O_3$ and $HfO_2$ in the oxide ceramic based on zirconia is at least 99.0 wt.-%. It is further preferred that the oxide ceramic based on zirconia comprises the following components in the indicated amounts:
$Y_2O_3$ 2.0 to 10.0 wt.-%, particularly 4.5 to 6.0 wt.-%;
$HfO_2$ up to 5.0 wt.-%;
$Al_2O_3$ up to 0.5 wt.-%;
$SiO_2$ up to 0.1 wt.-%; and
$Na_2O$ up to 0.1 wt.-%.

Typically the different layers of the blank have different colors. As used herein, the terms "color" and "colored" relate to the color, brightness and/or translucency of a layer.

"Translucency" is the light-transmitting capacity of a material, body or layer, i.e. the ratio of transmitted to incident light intensity.

Colors can also be characterized by their L*a*b values or by a color code commonly used in the dental industry. Examples of such color codes include Vitapan Classical® and Vita 3D Master®, both from VITA Zahnfabrik H. Rauter GmbH & Co. KG, and Chromascop® from Ivoclar Vivadent AG.

It is particularly preferred that the colors of the different layers are in the range of the colors of natural teeth.

The calculation of the coefficient of distortion should generally be based on a plurality of measurements of Vickers hardness at positions which cover each of the different layers of the blank. It is also possible to include measurements of Vickers hardness on interior surfaces of the blank that become accessible by cutting the blank into separate portions or discs. It is further preferred that the measurements cover a portion of the blank that is at least as large as a typical restoration to be manufactured from the blank.

According to one embodiment, the coefficient of distortion is calculated on the basis of measurements of $HV_{2.5}$ at measuring points which are distributed at a constant distance along a first line intercepting the different layers on an outer surface of the blank. Preferably, additional measuring points are distributed at a constant distance along a second line that is parallel to the first line on a surface in the center of the blank, which has been made accessible by cutting the blank. Further additional measuring points may be distributed at constant distance along lines connecting the upper and lower ends of the first and second lines.

It is particularly preferred that the constant distance between the measuring points along the first and second lines is not more than 5 mm. It is further preferred that the surface in the center of the blank has been made accessible by cutting the blank in half.

The $HV_{2.5}$ values of presintered ceramic materials for CAD/CAM applications are typically in the range of 300 to 1000 MPa.

In a second aspect, the invention also provides a multi-layer oxide ceramic green body for the manufacture of dental restorations comprising at least two different layers and having a coefficient of distortion $$d = \frac{(HV_{max} - HV_{min})}{\overline{HV}}$$

of less than 0.4, particularly less than 0.35, more particularly less than 0.3, preferably less than 0.25, more preferably less than 0.2 and most preferably less than 0.1, which coefficient is calculated on the basis of at least one measurement of $HV_{2.5}$ for each of the different layers, after a sintering step at a temperature in the range of 850 to 1350° C., particularly 900 to 1200° C., preferably 950 to 1150° C., more preferably 1000 to 1100° C. and most preferably at a temperature of about 1100° C.,
wherein:
$HV_{2.5}$ is the Vickers hardness measured at a load of 2.5 kgf (24.517 N) according to ISO 14705:2008;
$HV_{max}$ is the maximum of the measured values of $HV_{2-5}$;
$HV_{min}$ is the minimum of the measured values of $HV_{2.5}$; and
$\overline{HV}$ is the arithmetic mean of the measured values of $HV_{2.5}$.

The sintering step preferably comprises heating the green body at heating rates of 1 to 10 K/min, preferably 5 K/min, up to a temperature of 50 K below the desired sintering temperature and 1 to 3 K/min, preferably 1 K/min, up to the desired sintering temperature, preferably about 1100° C., and holding at this temperature for 30 to 480 min, preferably 120 min. In a particular embodiment, the sintering step comprises heating the green body at heating rates of 5 K/min up to a temperature of 50 K below the desired sintering temperature and 1 K/min up to the desired sintering temperature, preferably about 1100° C., and holding at this temperature for 120 min. If the green body comprises binder, the sintering step is typically preceded by a debinding step which preferably comprises heating at a heating rate of 0.1 to 0.5 K/min, preferably 0.1 to 0.3 K/min and more preferably 0.25 K/min, up to 300° C., 500° C. or 700° C. with holding times of 20 to 120 min, preferably 60 min, at 300° C. and/or 500° C. and/or 700° C. In a particular embodiment, the debinding step comprises heating at a heating rate of 0.25 K/min up to 700° C. with holding times of 60 min at 300° C., 500° C. and 700° C.

The term "green body" as used herein generally refers to an unsintered ceramic body, which has typically been prepared by compacting, such as compressing, oxide ceramic powders.

Preferred embodiments of the green body are as described above with regard to the presintered multi-layer oxide ceramic blank according to the first aspect of the invention. The green body is generally suitable as a precursor for this blank.

In a third aspect, the invention also provides a multi-layer oxide ceramic body for the manufacture of dental restorations comprising at least two different layers, wherein a sintering behavior of the at least two different layers is aligned to allow the ceramic body to be sintered without distortion.

In one preferred embodiment, the ceramic body is a presintered multi-layer oxide ceramic blank. In another preferred embodiment, the ceramic body is a multi-layer oxide ceramic green body. Further preferred embodiments of the oxide ceramic body are as described above with regard to the presintered multi-layer oxide ceramic blank according to the first aspect of the invention.

The sintering behavior is typically the relative linear shrinkage upon sintering at a temperature in the range of 850 to 1350° C., particularly 900 to 1200° C., preferably 950 to 1150° C., more preferably 1000 to 1100° C. and most preferably at a temperature of about 1100° C. The sintering preferably comprises heating the oxide ceramic materials at heating rates of 1 to 10 K/min, preferably 5 K/min, up to a temperature of 50 K below the desired sintering temperature and 1 to 3 K/min, preferably 1 K/min, up to the desired sintering temperature, preferably about 1100° C., and holding at this temperature for 30 to 480 min, preferably 120 min. In a particular embodiment, the sintering comprises heating the oxide ceramic materials at heating rates of 5 K/min up to a temperature of 50 K below the desired sintering temperature and 1 K/min up to the desired sintering temperature, preferably about 1100° C., and holding at this temperature for 120 min. If the oxide ceramic materials comprise binder, the sintering step is typically preceded by a debinding step which preferably comprises heating at a heating rate of 0.1 to 0.5 K/min, preferably 0.1 to 0.3 K/min and more preferably 0.25 K/min, up to 300° C., 500° C. or 700° C. with holding times of 20 to 120 min, preferably 60 min, at 300° C. and/or 500° C. and/or 700° C. In a particular embodiment, the debinding step comprises heating at a heating rate of 0.25 K/min up to 700° C. with holding times of 60 min at 300° C., 500° C. and 700° C.

It is also preferred that the sintering behavior of the at least two different layers is aligned such that the sintering behavior of the at least two different layers differ by less than 0.15%, particularly less than 0.10% and preferably less than 0.05%.

According to one embodiment, the sintering behavior of the at least two different layers is aligned in that at least one of these layers comprises a dopant incorporated therein. The dopant is typically selected from materials which do not have a significant coloring effect. The dopant is preferably selected from sintering aids and sintering inhibitors. Sintering aids are generally dopants which facilitate the sintering of an oxide ceramic material, thereby lowering the sintering temperature which is required to obtain a given degree of relative linear shrinkage. A preferred sintering aid is $Al_2O_3$. Sintering inhibitors are generally dopants which impede the sintering of an oxide ceramic material, thereby increasing the sintering temperature which is required to obtain a given degree of relative linear shrinkage. A preferred sintering inhibitor is $Y_2O_3$.

According to another embodiment, the sintering behavior of the at least two different layers is aligned in that different layers comprise oxide ceramic materials having different primary and/or secondary particle size and/or different specific surface area. Primary and secondary particle sizes are typically measured using image analysis methods such as transmission electron microscopy (TEM) or scanning electron microscopy (SEM). Specific surface areas are typically measured by gas adsorption according to the BET method.

According to yet another embodiment, the sintering behavior of the at least two different layers is aligned in that different layers have been subjected to different degrees of partial densification, and in particular by different degrees of powder compaction.

According to a particularly preferred embodiment, the sintering behavior of the at least two different layers is aligned by a combination of two or more of the above measures.

In a fourth aspect, the invention also provides a process for the manufacture of a multi-layer oxide ceramic body having at least two different layers which body can be sintered without distortion, wherein the process comprises aligning a sintering behavior of the different layers. In one preferred embodiment, the ceramic body is a presintered multi-layer oxide ceramic blank. In another preferred embodiment, the ceramic body is a multi-layer oxide ceramic green body. Further preferred embodiments of the oxide ceramic body are as described above with regard to the presintered multi-layer oxide ceramic blank according to the first aspect of the invention.

The process typically comprises the steps of:
(a) providing at least a first oxide ceramic material and a second oxide ceramic material, wherein the first oxide ceramic material and the second oxide ceramic material differ in terms of a sintering behavior; and
(b) adapting at least one of the oxide ceramic materials to align the sintering behavior of the first oxide ceramic material to the sintering behavior of the second oxide ceramic material.

In steps (a) and (b) defined above, the sintering behavior is typically the relative linear shrinkage upon sintering at a temperature in the range of 850 to 1350° C., particularly 900 to 1200° C., preferably 950 to 1150° C., more preferably 1000 to 1100° C. and most preferably at a temperature of about 1100° C. The sintering preferably comprises heating the oxide ceramic materials at heating rates of 1 to 10 K/min, preferably 5 K/min, up to a temperature of 50 K below the desired sintering temperature and 1 to 3 K/min, preferably 1 K/min, up to the desired sintering temperature, preferably about 1100° C., and holding at this temperature for 30 to 480 min, preferably 120 min. In a particular embodiment, the sintering comprises heating the oxide ceramic materials at heating rates of 5 K/min up to a temperature of 50 K below the desired sintering temperature and 1 K/min up to the desired sintering temperature, preferably about 1100° C., and holding at this temperature for 120 min.

It is also preferred that in step (a) the sintering behavior of the first oxide ceramic material and the sintering behavior of the second oxide ceramic material differ by at least 0.15%, particularly at least 0.25%, preferably at least 0.5% and more preferably more than 1.0%. It is also preferred that in step (b) the adapting results in the sintering behavior of the first oxide ceramic material and the sintering behavior of the second oxide ceramic material differing by less than 0.15%, particularly less than 0.10% and preferably less than 0.05%.

The process typically also comprises the steps of:
(c) forming layers of the oxide ceramic materials and arranging the layers on top of one another or forming a layer of the oxide ceramic materials which comprises a continuous gradient from the first oxide ceramic material to the second oxide ceramic material;
(d) optionally compacting, in particular compressing, the oxide ceramic materials to obtain a green body; and (e) optionally presintering the oxide ceramic materials to obtain a presintered ceramic blank.

According to one embodiment, adapting at least one of the oxide ceramic materials comprises incorporating a dopant into said oxide ceramic material. The dopant is typically selected from materials which do not have a significant coloring effect. The dopant is preferably selected from sintering aids and sintering inhibitors.

Sintering aids are generally dopants which facilitate the sintering an oxide ceramic material, thereby lowering the sintering temperature which is required to obtain a given degree of relative linear shrinkage. A preferred sintering aid is $Al_2O_3$. Sintering inhibitors are generally dopants which impede the sintering of an oxide ceramic material, thereby increasing the sintering temperature which is required to obtain a given degree of relative linear shrinkage. A preferred sintering inhibitor is $Y_2O_3$.

According to a preferred embodiment, a dopant can be selected to counteract the effect of additives such as coloring oxides which are already present in a layer. For instance, if the presence of additives in a particular layer of a ceramic body is causing a sintering facilitating effect, a sintering inhibitor like $Y_2O_3$ can be added to counteract this effect. If the presence of additives in a particular layer of a ceramic body is causing a sintering impeding effect, then a sintering aid like $Al_2O_3$ can be added to counteract this effect.

According to a preferred embodiment, the dopant is incorporated into the oxide ceramic material by coating the oxide ceramic material with the dopant, in particular with an aqueous solution of a water-soluble salt that can be converted to the dopant upon sintering, most preferably using a fluidized-bed apparatus. Nitrates and chlorides are particularly preferred.

According to another embodiment, adapting at least one of the oxide ceramic materials comprises changing the primary and/or secondary particle size and/or the specific surface area of at least a portion of said oxide ceramic material. Primary and secondary particle sizes are typically measured using image analysis methods such as transmission electron microscopy (TEM) or scanning electron microscopy (SEM). Specific surface areas are typically measured by gas adsorption according to the BET method.

According to yet another embodiment, adapting at least one of the oxide ceramic materials comprises subjecting said oxide ceramic materials to different degrees of partial densification. This can be achieved for instance by compacting and in particular compressing different layers at different pressures independently of one another and then combining these layers. It is also possible to introduce a first layer into a pressing die and subjecting said layer to a first pressure, and then introducing at least one further layer into the same pressing die on top of the first layer and subjecting to a second pressure which is lower than the first pressure.

According to a particularly preferred embodiment, aligning the sintering properties of the different layers comprises a combination of two or more of the above measures.

In a fifth aspect the invention also relates to a multi-layer oxide ceramic body obtainable by the process of the fourth aspect. Preferred embodiments of the oxide ceramic body are as described above with regard to the presintered multi-layer oxide ceramic blank according to the first aspect of the invention.

The multi-layer oxide ceramic bodies according to the invention are particularly suitable for the manufacture of dental restorations. Accordingly, in a sixth aspect the invention also relates to a process for the manufacture of a dental restoration, which comprises using a multi-layer ceramic body, such as a presintered multi-layer ceramic blank or a multi-layer ceramic green body, as defined above for the preceding aspects of the invention.

The process for the manufacture of a dental restoration preferably comprises shaping the multi-layer ceramic body, in particular the presintered multi-layer ceramic blank, to a desired geometry to obtain a shaped ceramic product. It is preferred that the shaping is carried out by machining. The machining is typically controlled by a computer, preferably using a CAD/CAM process.

According to a preferred embodiment, the shaped ceramic product has the shape of a dental framework, abutment or monolithic full-contour dental restoration, in particular a multi-unit dental restoration.

It is further preferred that the process also comprises densely sintering the shaped ceramic product to obtain a dental restoration.

The invention is explained in more detail below on the basis of examples.

EXAMPLES

General Procedure for Coating Oxide Powders with Colorants and/or Dopants

An aqueous solution containing suitable amounts of water-soluble salts of the elements to be coated onto the oxide powder and 0.1-2 wt.-% (relative to the quantity of powder to be coated) of a water-soluble binder such as polyvinyl alcohol (e.g. Optapix PAF2 or PAF35 from the company Zschimmer & Schwarz) was homogenized by stirring (using e.g. a magnetic stirrer) for about 0.5 h. The obtained solution was applied completely onto the oxide powder by means of a fluidized-bed granulator. During this step the powder was kept in suspension as a fluidized bed by means of compressed air (0.15-0.30 bar, 30-80° C.), and the coloring solution was applied to the powder through a nozzle which was arranged above this fluidized bed by spraying at a spraying pressure of 2 to 6 bar. The heated compressed air provided for a simultaneous drying of the coated powder during the process.

Example 1

Control of Shrinkage Properties by Adding Dopants (i.e. Non-Coloring Sintering Aids or Sintering Inhibitors) to Colored or Uncolored Powders:

Basic oxide powders were obtained by optionally coating a raw zirconia powder (TOSOH TZ-3YSB-C) with nitrate salts of coloring elements using the general procedure as indicated in the table below.

| Powder | Raw powder | Coloring elements[1] |
|---|---|---|
| White | TOSOH TZ-3YSB-C[2] | — |
| MO2 | TOSOH TZ-3YSB-C[2] | 0.06 wt.-% Fe (calculated as $Fe_2O_3$) |
| | | 0.0015 wt.-% Pr (calculated as $Pr_2O_3$) |
| | | 0.0008 wt.-% Mn (calculated as $Mn_2O_3$) |
| | | 0.0004 wt.-% Tb (calculated as $Tb_2O_3$) |

[1] based on the total mass of the oxide mixture after sintering
[2] comprising 3 wt.-% $Y_2O_3$ and 0.25 wt.-% $Al_2O_3$ Doped oxide powders were prepared by further coating the basic powders with nitrate salts of Y or Al using the general procedure as indicated in the table below.

| Powder | Basic powder | Dopant[1] |
|---|---|---|
| White-1 | White | — |
| White-2 | White | 0.05 wt % Al (calculated as $Al_2O_3$) |
| MO2-1 | MO2 | — |
| MO2-2 | MO2 | 0.02 wt % Y (calculated as $Y_2O_3$) |
| MO2-3 | MO2 | 0.1 wt % Y (calculated as $Y_2O_3$) |
| MO2-4 | MO2 | 0.5 wt % Y (calculated as $Y_2O_3$) |

[1]based on the total mass of the oxide mixture after sintering

The doped oxide powders were cold uniaxially pressed at 100-250 MPa, debinded at 500° C. and subjected to a heat treatment over a temperature range of 950 to 1150° C. at heating rates of 5 K/min up to 900° C. and 1 K/min up to 1150° C. A plot of the relative shrinkage as a function of temperature is shown in FIG. 1.

As can be seen from this figure, adding 0.5 wt % of the sintering inhibitor $Y_2O_3$ to the undoped colored powder MO2-1 to obtain the doped colored powder MO2-4 increased the presintering temperature required to obtain a relative linear shrinkage of 1% by about 18° C. Adding 0.05 wt % of the sintering aid $Al_2O_3$ to the undoped uncolored powder White-1 to obtain the doped uncolored powder White-2 decreased the presintering temperature required to obtain a relative linear shrinkage of 1% by about 5° C. By combining doped and undoped powders or differently doped powders in different layers, the shrinkage at a given sintering temperature can be equalized so that a multi-layer block made from these powders does not show distortion in the presintered or densely sintered state.

Example 2

Presintered Multi-Layer Oxide Ceramic Blocks Using Doped Oxide Ceramic Powders

Blocks (40±1 mm×15.5±0.5 mm×19±1 mm) of types A and B as indicated in the following table were prepared by successively introducing oxide powders according to Example 1, or mixtures of such powders, into a pressing die to obtain a series of layers and uniaxially pressing the powders at 100 to 150 MPa to obtain green bodies. Three bodies each of types A and B were prepared.

| | | Composition | |
|---|---|---|---|
| Layer | Relative height | Block A (comparative) | Block B |
| Layer 1 (bottom) | 50% | MO2-1 | MO2-4 |
| Layer 2 (middle) | 25% | 60% MO2-1 40% White-1 | 60% MO2-4 40% White-2 |
| Layer 3 (top) | 25% | White-1 | White-2 |

The green bodies were then transferred to a muffle furnace, with each of the three bodies of the same type being placed onto the refractory cordierite setter plate in a different orientation so as to exclude that any distortion observed in the obtained presintered blanks is merely due to temperature inhomogeneity within the furnace. The green bodies were subjected to the following temperature program for debinding and presintering:
0.25 K/min up to 300° C., holding time 60 min
0.25 K/min up to 500° C.
1 K/min up to 1120° C., holding time 120 min.

After presintering, the three blocks of the same type were brought into the same orientation and bonded to each other via their face planes in order to more clearly illustrate any deformation.

Figure 2A:
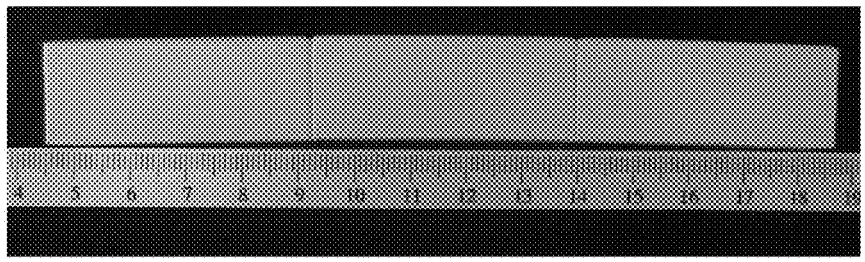
FIG. 2A shows a photograph of bonded presintered blocks.
Figure 2B:
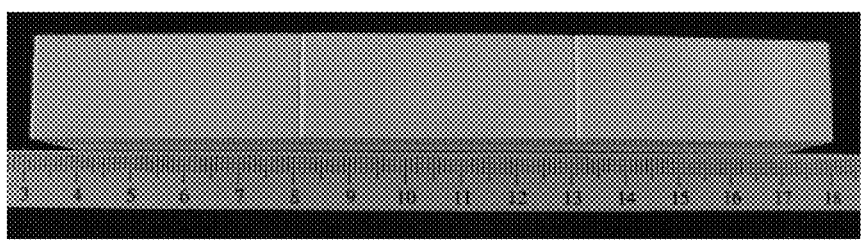
FIG. 2B shows a photograph of bonded presintered blocks.

Photographs of the bonded presintered blocks are shown in FIGS. 2A (blocks of type A) and 2B (blocks of type B), wherein the main line of sight is parallel to the arrangement of the different layers. A straight scale was placed next to the blocks for illustration. The comparative presintered blocks of type A using only undoped oxide ceramic powders were found to be distorted, whereas the presintered blocks of type B using doped oxide ceramic powders were found not to be distorted.

Example 3

Determination of the Coefficient of Distortion

Figure 3:
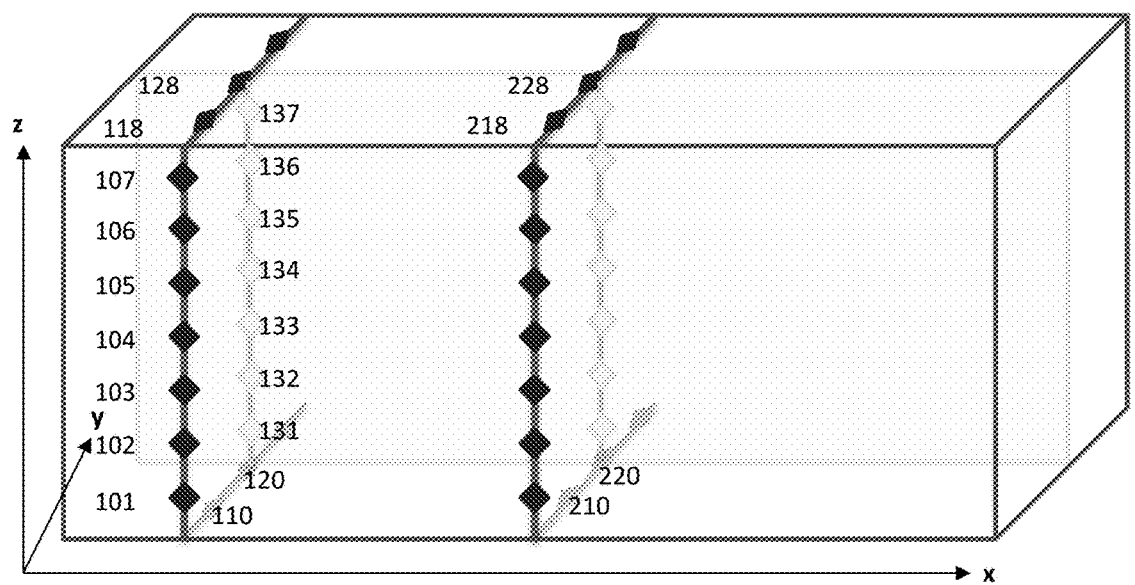
FIG. 3 shows locations of measuring points of Vickers hardness for blocks.

Vickers hardness $HV_{2.5}$ (0.5-1.0 GPa) was measured at a plurality of measuring points of the presintered blocks of types A and B as obtained in Examples 2A and 2B. The locations of the measuring points are schematically indicated in FIG. 3, wherein z is the dimension in which the different layers are arranged. The results are given in the following table:

| | | $HV_{2.5}$ (0.5-1.0 GPa) | |
|---|---|---|---|
| Surface | Coordinates[1] | Block A (comparative) | Block B |
| Side | 101 | 784 | 734 |
| | 102 | 743 | 690 |
| | 103 | 703 | 655 |
| | 104 | 616 | 579 |
| | 105 | 621 | 650 |
| | 106 | 859 | 687 |
| | 107 | 901 | 721 |
| Bottom | 110 | 579 | 682 |
| | 120 | 579 | 681 |
| Top | 118 | 734 | 680 |
| | 128 | 674 | 680 |
| Center | 131 | | 724 |
| | 132 | 787 | 690 |
| | 133 | 663 | 646 |
| | 134 | 521 | 575 |
| | 135 | 647 | 653 |
| | 136 | 715 | 694 |
| | 137 | 839 | 737 |
| Bottom | 210 | 579 | 690 |
| | 220 | 575 | 672 |
| Top | 218 | 683 | |
| | 228 | 727 | |

[1]as indicated in FIG. 3

Figure 4A:
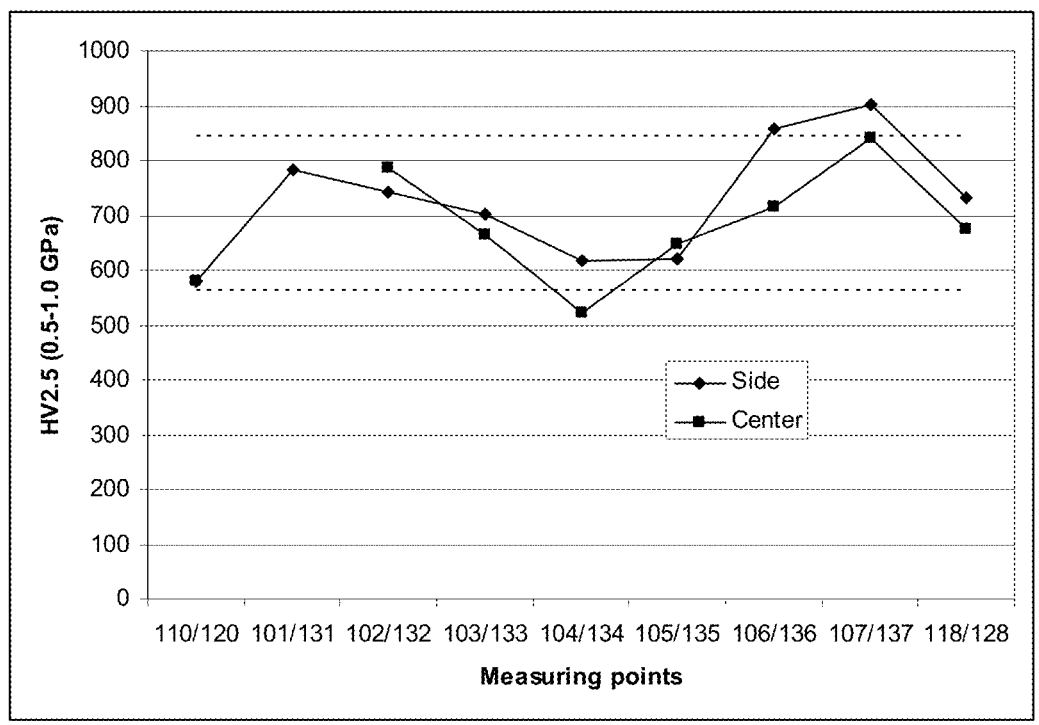
FIG. 4A shows hardness values for blocks measured at coordinates 101 to 137.
Figure 4B:
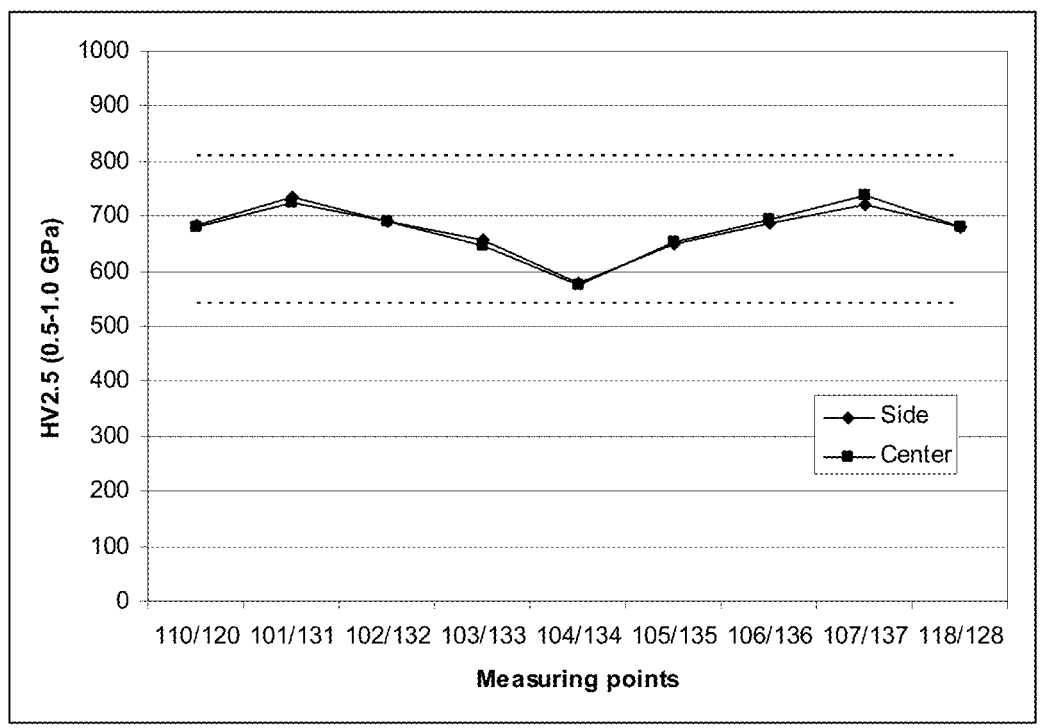
FIG. 4B shows hardness values for blocks measured at coordinates 101 to 137.

The hardness values measured at coordinates 101 to 137 are further illustrated in FIGS. 4A (Block A) and 4B (Block B). In these figures, the dashed lines illustrate the range of hardness values providing for a coefficient of distortion of d=0.4.

Block A showed an asymmetric distribution and high variance of hardness values. The coefficient of distortion was determined to be d=0.539. Such a level of distortion is not acceptable for the application as a CAD/CAM block. Dental frameworks prepared from such a block will exhibit a very bad accuracy of fit.

In contrast to this, Block B showed a symmetric distribution of hardness values which merely reflects the pressure inhomogeneity that occurs during the pressing step. The overall variance of hardness values was low. The coefficient of distortion was determined to be d=0.238. Such a level of distortion is acceptable for the application as a CAD/CAM block, and dental frameworks prepared from such a block will exhibit a good accuracy of fit.

Example 4

Figure 5:
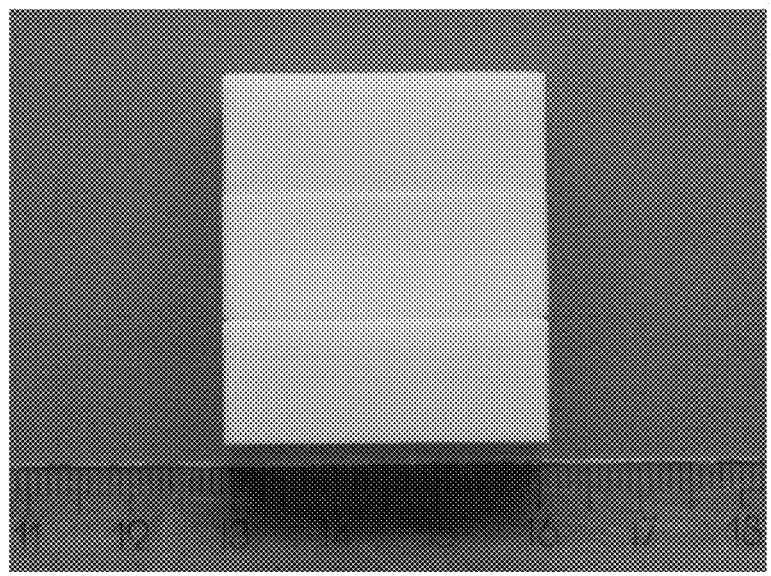
FIG. 5 shows a photograph of fully sintered blocks.

Fully Sintered Multi-Layer Oxide Ceramic Blocks Using Doped Oxide Ceramic Powders Three blocks (31.5 mm×12.5 mm×15.3 mm) were prepared by preparing presintered blocks of type B as described in Example 2 and fully sintering these blocks at 1500° C., holding time 30 min. After sintering, the blocks were placed on top of one another. Photographs of the obtained blocks are shown in FIG. 5, wherein the main line of sight is parallel to the arrangement of the different layers. Even in the finally densified state the blocks of type B using doped oxide ceramic powders did not show distortion.

Example 5 (Comparative)

Bi-layer blocks (29 mm×4.6 mm×5.8 mm) were prepared from oxide powders derived from two different raw zirconia powders, one of which was coated with coloring elements using the general procedure as indicated in the table below.

| Powder | Raw powder | Coloring elements[1] |
|---|---|---|
| White | TOSOH Zpex[2] | — |
| Shaded | KCM KZ-3YF(SD)-AC[3] | 0.06 wt % Fe (calculated as $Fe_2O_3$) |
| | | 0.0015 wt % Pr (calculated as $Pr_2O_3$) |
| | | 0.0008 wt % Mn (calculated as $Mn_2O_3$) |
| | | 0.0004 wt % Tb (calculated as $Tb_2O_3$) |

Figure 6:
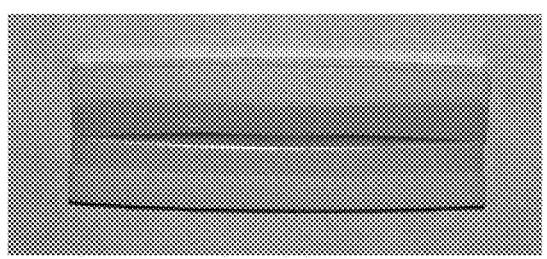
FIG. 6 shows a photograph of presintered blocks.

[1] based on the total mass of the oxide mixture after sintering
[2] comprising 0.05 wt.-% $Al_2O_3$; specific surface area ~13 $m^2/g$
[3] comprising 0.25 wt.-% $Al_2O_3$; specific surface area ~7 $m^2/g$ The two oxide powders were successively introduced into a pressing die and uniaxially pressed at 150 to 200 MPa to obtain a bi-layer green body and then presintered using the following firing cycle:
0.25 K/min up to 300° C., holding time 120 min
0.25 K/min up to 500° C.
0.5 K/min up to 700° C., holding time 120 min
1 K/min up to 1050° C., holding time 120 min Photographs of the obtained blocks are shown in FIG. 6. The blocks were found to be distorted and curved towards the uncolored layer, i.e. the layer which contained the zirconia powder of higher specific surface area.

Example 6

Four elongated rectangular blocks (46 mm×7.5 mm×5.8 mm) simulating 4-unit monolithic bridges comprising two layers, white and shaded, were fabricated from Y-TZP zirconia powders formulated as per the table below. Two layers of powders were sequentially poured into a simple steel channel mold on a vibration table to assure a reasonably flat interface between the layers and were uniaxially compacted using a pressure of about 18 MPa. The obtained uniaxially pre-pressed green compacts were vacuum sealed in latex bags and additionally cold isostatically pressed at about 345 MPa and finally sintered at 1500° C. for 2 h. Visual observations on the absence or presence of distortion/curvature are summarized in the table below.

| Bilayer Block Composition wt.-% | | Example 6A | Example 6B | Example 6C | Example 6D |
|---|---|---|---|---|---|
| Layer 1 (white) | TOSOH Zpex[1] | 100 | 100 | 100 | 80 |
| | TOSOH 3YSB-E[2] | — | — | — | 20 |
| Layer 2 (shaded) | TOSOH Zpex[1] | 70 | 55 | 80 | 80 |
| | TOSOH 3YSB-E[2] | — | 15 | — | — |
| | TOSOH Zpex Yellow[3] | 30 | 30 | — | — |
| | TOSOH TZ-Yellow-SB-E[4] | — | — | 20 | 20 |
| Visible distortion/curvature | | Curved towards yellow | Nearly absent | Curved towards white | Nearly absent |

[1] comprising 0 wt.-% $Fe_2O_3$; specific surface area ~13 $m^2/g$
[2] comprising 0 wt.-% $Fe_2O_3$; specific surface area ~7 $m^2/g$
[3] comprising 0.14 wt.-% $Fe_2O_3$; specific surface area ~13 $m^2/g$
[4] comprising 0.19 wt.-% $Fe_2O_3$; specific surface area ~7 $m^2/g$ As illustrated by these results, by adapting the specific surface areas of the powders or powder mixtures used in different layers, the shrinkage behavior of the powders in those layers can be equalized to prevent distortion. More particularly, by combining different powders of similar chemical composition but different specific surface area either within the shaded layer (Example 6B) or the white layer (Example 6D), the specific surface area of the resulting powder mixture can be equalized with that of the other layer so as to effectively prevent distortion in the presintered and densely sintered states.

Example 7

Sintering Behavior of Differently Predensified Powders

Figure 7:
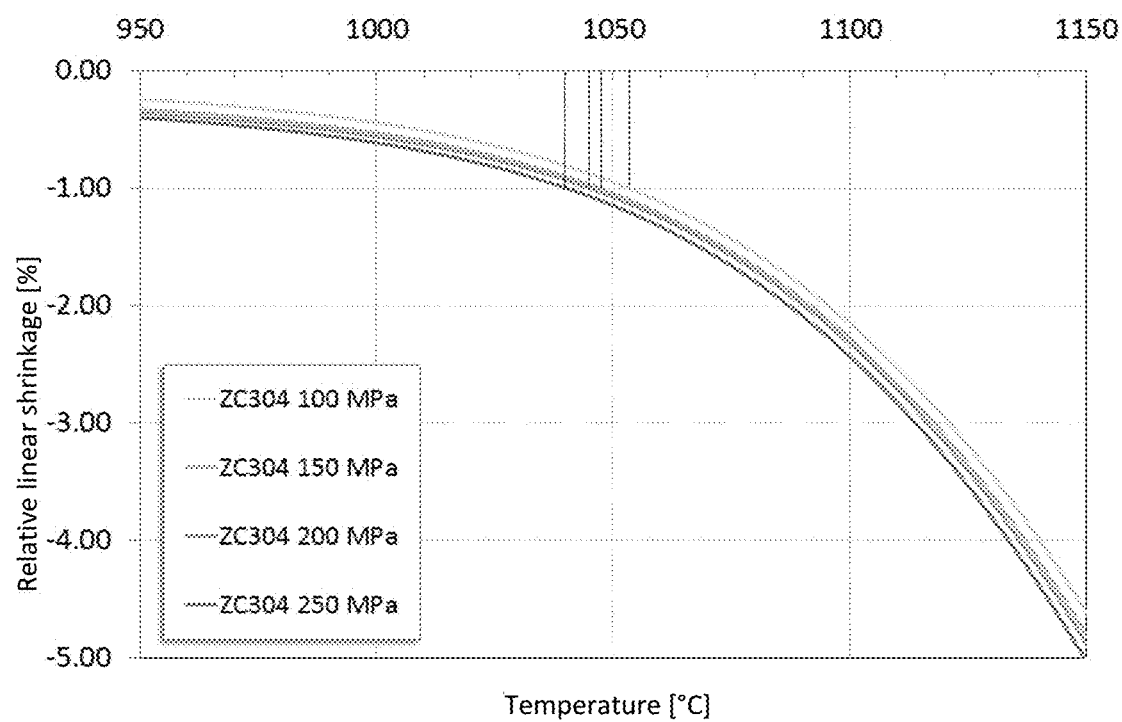
FIG. 7 shows a plot of the relative shrinkage as a function of temperature.

Samples of a zirconia ceramic powder (KCM KZ-3YF (SD)AC) were cold uniaxially pressed at pressures of 100, 150, 200 and 250 MPa and debinded at 500° C. The obtained densified powders were subjected to a heat treatment over a temperature range of 950 to 1150° C. at heating rates of 5 K/min up to 900° C. and 1 K/min up to 1150° C. A plot of the relative shrinkage as a function of temperature is shown in FIG. 7. As can be seen from this figure, the sintering behavior of oxide ceramic powders can be adapted by subjecting said powders to different degrees of partial densification. By subjecting the powders to be used in different layers to different degrees of partial densification, their linear shrinkage at a given sintering temperature can be equalized so that a multi-layer block made from these powders does not show distortion in the presintered or densely sintered state.

The invention claimed is:

1. Process for the manufacture of a multi-layer oxide ceramic body having at least two different layers which body can be sintered without distortion, wherein the process comprises
   (a) providing at least a first oxide ceramic material and a second oxide ceramic material, wherein the first oxide ceramic material and the second oxide ceramic material differ in terms of a sintering behavior and wherein at least one of the oxide ceramic materials comprises one or more coloring elements; and (b) equalizing a sintering behavior of the first oxide ceramic material to a sintering behavior of the second oxide ceramic material by coating at least one of the oxide ceramic materials with a dopant, wherein in each case the sintering behavior is the relative linear shrinkage upon sintering at a temperature in the range of 850 to 1350° C.

2. Process according to claim 1, wherein the body is suitable for the manufacture of a multi-unit dental restoration comprising two or more units.

3. Process according to claim 1, wherein the at least two different layers differ in terms of chemical composition.

4. Process according to claim 1, wherein the at least two different layers have different colors and wherein the colors are in the range of the colors of natural teeth.

5. Process according to claim 1, wherein the sintering behavior is the relative linear shrinkage upon sintering at a temperature in the range of 900 to 1200° C.

6. Process according to claim 1, wherein in step (a) the sintering behavior of the first oxide ceramic material and the sintering behavior of the second oxide ceramic material differ by at least 0.15%.

7. Process according to claim 1, wherein in step (b) the equalizing results in the sintering behavior of the first oxide ceramic material and the sintering behavior of the second oxide ceramic material differing by less than 0.15%.

8. Process according to claim 1, wherein said dopant is selected from sintering aids and sintering inhibitors.

9. Process according to claim 8, wherein said sintering aids comprise $Al_2O_3$ and said sintering inhibitors comprise $Y_2O_3$.

10. Process according to claim 1, wherein equalizing a sintering behavior of the first oxide ceramic material to a sintering behavior of the second oxide ceramic material further comprises changing a primary and/or secondary particle size and/or a specific surface area of at least a portion of said at least one oxide ceramic material.

11. Process according to claim 1, wherein equalizing a sintering behavior of the first oxide ceramic material to a sintering behavior of the second oxide ceramic material further comprises subjecting said oxide ceramic materials to different degrees of partial densification.

12. Process according to claim 1 which further comprises (c) forming layers of the oxide ceramic materials and arranging the layers on top of one another or forming a layer of the oxide ceramic materials which comprises a continuous gradient from the first oxide ceramic material to the second oxide ceramic material;

(d) optionally compacting or compressing the oxide ceramic materials to obtain a green body; and (e) optionally presintering the oxide ceramic materials to obtain a presintered ceramic blank.

13. Process for the manufacture of a dental restoration, which process comprises preparing a multi-layer oxide ceramic body by the process according to claim 1 and shaping the body to a desired geometry to obtain a shaped ceramic product.

14. Process according to claim 13, wherein the shaping is carried out by machining.

15. Process according to claim 13, wherein the shaped ceramic product has the shape of a dental framework, abutment or monolithic full-contour dental restoration.

16. Process according to claim 13 further comprising densely sintering the shaped ceramic product.

* * * * *